(12) United States Patent
Potts

(10) Patent No.: US 10,191,053 B2
(45) Date of Patent: *Jan. 29, 2019

(54) METHODS FOR MEASURING AND REPORTING VASCULARITY IN A TISSUE SAMPLE

(71) Applicant: Flagship Biosciences, Inc., Westminster, CO (US)

(72) Inventor: Steven J. Potts, Anthem, AZ (US)

(73) Assignee: Flagship Biosciences, Inc., Westminster, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/642,249

(22) Filed: Jul. 5, 2017

(65) Prior Publication Data

US 2017/0298434 A1 Oct. 19, 2017

Related U.S. Application Data

(63) Continuation of application No. 14/588,319, filed on Dec. 31, 2014, now Pat. No. 9,725,766.
(Continued)

(51) Int. Cl.
*G06T 7/00* (2017.01)
*G06K 9/00* (2006.01)
(Continued)

(52) U.S. Cl.
CPC ... *G01N 33/56966* (2013.01); *G01N 33/5044* (2013.01); *G01N 33/5064* (2013.01); *G01N 33/56972* (2013.01); *G06K 9/00127* (2013.01); *G06T 7/0012* (2013.01); *G01N 2800/7014* (2013.01); *G01N 2800/7038* (2013.01);
(Continued)

(58) Field of Classification Search
CPC ....... G01N 33/56966; G01N 33/56972; G01N 33/5044; G01N 33/5064; G01N 2800/7038; G01N 2800/7014; G06T 7/0012; G06T 2207/10056; G06T 2207/30101;
(Continued)

(56) References Cited

U.S. PATENT DOCUMENTS 9,725,766 B1 * 8/2017 Potts .................... C12Q 1/6876
2003/0165263 A1 9/2003 Hamer et al.
(Continued)

OTHER PUBLICATIONS

Powner et al. "Visualization of Gene Expression in Whole Mouse Retina by in situ Hybridization." Nature Protocols, vol. 7, No. 6, 2012, pp. 1086-1096.*

*Primary Examiner* — Jon Chang
(74) *Attorney, Agent, or Firm* — Josiah Barbour

(57) ABSTRACT

The disclosure concerns a method for measuring and reporting vascularity in a biological tissue sample. The method generally includes: within a digital image of a tissue section, (i) identifying endothelial cells, lymphatic cells, or a combination thereof; (ii) mapping one or more proximity regions, each of the proximity regions defining an area between detected vessels and a first distance outwardly therefrom; and (iii) calculating one or more of: a vessel proximity score or a hypoxia score, wherein the vessel proximity score relates a composition of objects within the proximity regions, and wherein the hypoxia score relates a composition of tissue within or outside of the proximity regions, respectively.

16 Claims, 2 Drawing Sheets

Related U.S. Application Data

(60) Provisional application No. 62/030,518, filed on Jul. 29, 2014.

(51) Int. Cl.
*G01N 33/569* (2006.01)
*G01N 33/50* (2006.01)

(52) U.S. Cl.
CPC ............... *G06T 2207/10024* (2013.01); *G06T 2207/10056* (2013.01); *G06T 2207/30024* (2013.01); *G06T 2207/30101* (2013.01)

(58) Field of Classification Search
CPC G06T 2207/10024; G06T 2207/30024; G06K 9/00127
See application file for complete search history.

(56) References Cited

U.S. PATENT DOCUMENTS

| | | |
|---|---|---|
| 2011/0103657 A1 | 5/2011 | Kang et al. |
| 2012/0076390 A1 | 3/2012 | Potts et al. |
| 2014/0003702 A1* | 1/2014 | McCulloch ........... G06T 7/0012 382/134 |
| 2014/0105824 A1 | 4/2014 | Shepard et al. |
| 2015/0004630 A1 | 1/2015 | Lange et al. |
| 2015/0290250 A1 | 10/2015 | Zhou et al. |

* cited by examiner

METHODS FOR MEASURING AND REPORTING VASCULARITY IN A TISSUE SAMPLE

CROSS-REFERENCE TO RELATED APPLICATIONS

This application is a continuation of U.S. Ser. No. 14/588,319, filed Dec. 31, 2014, titled "METHODS FOR MEASURING AND REPORTING VASCULARITY IN A TISSUE SAMPLE";

which claims benefit of priority with U.S. Provisional Ser. No. 62/030,518, filed Jul. 29, 2014;

the entire contents of each of which are hereby incorporated by reference.

BACKGROUND OF THE INVENTION

Field of the Invention

This invention relates to methods for measuring and reporting vascularity in a tissue sample; and more particularly, to methods for evaluation of angiogenesis and hypoxia using digital image analysis platforms.

Related Art

The ability to evaluate the vascular structure of tissue is important in many therapeutic areas, both in areas that seek to increase the growth of blood vessels (pro-angiogenic) and areas that seek to decrease or shrink blood vessels (anti-angiogenic). It is important to be able to evaluate the architecture of the blood vasculature, as well as to determine how adequately blood supply, nutrients, and oxygen are being made available to local tissue, and how adequately waste products are being removed.

Angiogenesis is a biological process of generating new blood vessels from pre-existing blood vessels into a tissue or organ. Under normal physiology, angiogenesis is tightly regulated by many angiogenic factors, and switching of the phenotype depends on a net balance between up-regulation of angiogenic stimulators and down-regulation of angiogenic suppressors. Therapeutic areas where interventions serve to modulate angiogenesis include: atherogenesis, arthritis, psoriasis, oncology, corneal neovascularization, and diabetic retinopathy.

Evaluation of angiogenesis therapy requires measuring the changes on the tissue vasculature. This is made difficult in that it must either be studied: (i) non-invasively, using radiologic or other non-destructive imaging modalities; (ii) evaluated with histopathology using tissue sections; or (iii) with lab assays with two-dimensional and three-dimensional cell cultures. Histopathology provides the highest resolution evaluation of actual tissue architecture, but quantitation requires measurements on a thin section of a three-dimensional blood vessel network.

Over many years, manual and semi-automated approaches have been developed to measure the number and morphometry of endothelial stained vessels in tissue histology sections. There are a wide number of antibodies that have been developed against both endothelial cells as well as other cells associated with vasculature (e.g. smooth muscle actin), or specific subsets of developing endothelial cells. These can be stained using either immunohistochemistry (IHC) techniques or immunofluorescent (IF) techniques, either singly or in combination with other multiplex stains.

A manual technique to evaluate vascularity in tissue samples was described in Brem, S., R. Cotran, and J. Folan, "*Tumor angiogenesis: a quantitative method for histologic grading*", Journal of the National Cancer Institute, 1972. 48(2): p. 347-356. The technique provides a subjective composite rating of 0-100 based on vasoproliferation, endothelial cell hyperplasia, and endothelial cytology.

Weidner developed a micro-vessel density (MVD) approach in 1991, as described in Weidner, N., et al., "*Tumor angiogenesis and metastasis—correlation in invasive breast carcinoma*", New England Journal of Medicine, 1991. 324 (1): p. 1-8. In Weidner, the tissue was surveyed with a 4× objective, and the areas with the most vascularization, or "hotspots" were identified. In these areas, the field of view with the highest vascularization was then counted for vessels with a 20× or 40× objective. Then the second highest field of view is counted, and up to ten fields of view are tabulated in this fashion. Thus, these "hotspot" areas, or areas which appear to an observer to have high vascularity, are chosen by the observer and then micro-vessel density is computed. While studies have ranged from 3 to 5 fields of view or more, most studies utilize the average of the three most vascularized fields of view when reporting results. The counting method itself can be made slightly more objective after the hotspot regions of interest are selected by evaluating the fields of view by using a Chalkey grid eyepiece as suggested in Chalkley, H., "*Method for the quantitative morphologic analysis of tissues*", Journal of the National Cancer Institute, 1943. 4(1): p. 47-53; and Fox, S. B., et al., "*Tumor angiogenesis in node-negative breast carcinomas—relationship with epidermal growth factor receptor, estrogen receptor, and survival*", Breast cancer research and treatment, 1994. 29(1): p. 109-116. While the methodology overlaps, and both critically depend on evaluating and selecting "hotspots", the Chalkey method can be considered a correlate for vessel area, while MVD is more of a correlate for vessel density.

The field and number of investigations using methodology related to this approach grew tremendously in the following ten years. A review paper of MVD limited only to breast carcinoma studies illustrates this growth. In 2002, forty-three independent previous studies linking micro-vessel density to clinical outcome in breast cancer were reviewed, and the clinical utility of the method confirmed as a prognostic factor; see Uzzan, B., et al., "*Microvessel Density as a Prognostic Factor in Women with Breast Cancer A Systematic Review of the Literature and Meta-Analysis*", Cancer research, 2004. 64(9): p. 2941-2955. Factor VIII was used in twenty seven of these studies, CD31 in ten, and CD34 in eight. The majority (thirty-nine of forty-three) included measurement from the technique developed by Weidner, three studies included Chalkey methods, and seven studies utilized image analysis for an area based method. In these publications, the authors stress the need for better standardization in MVD, as there was high degree of variability in the number of fields observed, and the exact methodology of the counting technique.

The extent that a human observer is unreliable in estimating and identifying hotspots is well illustrated from a paper evaluating MVD in breast carcinomas. In these studies, the manual technique from Weidner was followed, with the observer identifying and then counting vessels in order, for what was perceived as the ten vascularized highest microscope fields of view. The first field counted actually contained the greatest number of microvessels in only 20% of the sections. In the apparent highest five fields identified by observer, the highest field of view was only found in these five fields sixty-five percent of the time; see Martin, L., et al., "*Examining the technique of angiogenesis assessment in invasive breast cancer*", British journal of cancer, 1997. 76(8): p. 1046.

Multiple researchers have undertaken to use image analysis for removing the observer variability introduced when attempting to identify hotspots. Van der Laak, J., et al., "*An improved procedure to quantify tumor vascularity using true color image analysis: comparison with the manual hot-spot procedure in a human melanoma xenograft model*", J. Pathol, 1998. 184: p. 136-143, describes a semi-automated technique which acquired all fields of view from a tissue section, and then identified hotspots based on the higher areas of positive endothelial staining. The technique was improved upon with the introduction of image analysis morphology to use number of vessels per field rather than area when choosing hotspots; see Belien, J., et al., "*Fully automated microvessel counting and hot spot selection by image processing of whole tumor sections in invasive breast cancer*", Journal of clinical pathology, 1999. 52(3): p. 184-192.

Microvessel density, Chalkey counts, and image analysis methods were analyzed in depth and correlations between MVD and Chalkey counts, both relying on the "hot spot" approach, were compared. The use of two versus three fields of view with Chalkey counts was evaluated, and the degree of correlation (r=0.93) was considered high enough that only two fields was recommended as sufficient, although using the top two versus top three fields of view will generally produce slightly higher average values as described in Offersen, B., M. Borre, and J. Overgaard, "*Quantification of angiogenesis as a prognostic marker in human carcinomas: a critical evaluation of histopathological methods for estimation of vascular density*", European Journal of Cancer, 2003. 39(7): p. 881-890. This publication further evaluated the prognostic ability comparison between MVD and Chalkey in large cohorts of prostate, breast, bladder, and non-small cell lung carcinomas.

More recent studies are more likely to include image analysis based total microvascular area (TVA) along with MVD counts, see Sharma, S., M. Sharma, and C. Sarkar, "*Morphology of angiogenesis in human cancer: a conceptual overview, histoprognostic perspective and significance of neoangiogenesis*", Histopathology, 2005. 46(5): p. 481-489. Total microvascular area predates digital pathology, and TVA, MVD, and Chalkey counts all use the same approach with selecting hotspots and several fields of view.

Referring to Hansen, S., et al., "*Angiogenesis in breast cancer: a comparative study of the observer variability of methods for determining microvessel density*", Laboratory investigation; a journal of technical methods and pathology, 1998. 78(12): p. 1563, microvessel density, vascular area, Chalkey counting, and stereological area of vascular profiles were compared in breast cancer. The authors found highest reproducibility in Chalkey counting and stereology, and recommend Chalkey counting overall. Earlier, microvessel density, Chalkey count, and area-based computer image analysis were compared in breast carcinomas, with the authors recommending Chalkey counts; see Fox, S. B., et al., "*Quantitation and prognostic value of breast cancer angiogenesis: comparison of microvessel density, Chalkey count, and computer image analysis*", The Journal of pathology, 1995. 177(3): p. 275-283.

In the analyzed hotspots, some researchers have looked at other image-analysis based measurements of individual vessels. These have included major axis length, minor axis length, perimeter, compactness (perimeter/area), and more esoteric measurements like shape factor and Feret diameter; see Korkolopoulou, P., et al., "*Clinicopathologic correlations of bone marrow angiogenesis in chronic myeloid leukemia: a morphometric study*", Leukemia, 2003. 17(1): p. 89-97; and Korkolopoulou, P., et al., "*A morphometric study of bone marrow angiogenesis in hairy cell leukemia with clinicopathological correlations*", British journal of hematology, 2003. 122(6): p. 900-910.

One researcher derived five classes of microvessel patterns in breast carcinomas and used these for stratification and prognostic outcome. The five classes were (a) increased, blood-filled capillaries with some clustering in the tumor; (b) small-sized capillaries in the tumor; (c) small-sized capillaries condensing at the periphery of the tumor (d); compressed delicate capillaries in the tumor; and (e) compressed delicate capillaries surrounding the tumor islands; see Safali, M., et al., "*A distinct microvascular pattern accompanied by aggressive clinical course in breast carcinomas: A fact or a coincidence?*", Pathology-Research and Practice, 2010. 206(2): p. 93-97.

Researchers have noted that heterogeneity of vascularity, as measured by the coefficients of variation of microvessel density or area in randomly sampled regions, is lower in tumors compared to normal tissues in prostate; see Van Niekerk, C. G., et al., "*Computerized whole slide quantification shows increased microvascular density in pT2 prostate cancer as compared to normal prostate tissue*", The Prostate, 2009. 69(1): p. 62-69; and Bigler, S. A., R. E. Deering, and M. K. Brawer, "*Comparison of microscopic vascularity in benign and malignant prostate tissue*", Human pathology, 1993. 24(2): p. 220-226. This may be explained by strongly increased levels of angiogenic factors that result in a saturation of the vascular bed. Vessel density may actually exceed metabolic requirements in tumors, and the result is uniform over vascularization; Hlatky, L., P. Hahnfeldt, and J. Folkman, "*Clinical application of antiangiogenic therapy: microvessel density, what it does and doesn't tell us*", J Natl Cancer Inst, 2002. 94(12): p. 883-93.

With the introduction of digital pathology, the entire slide is available as a digital image for image analysis. This is a vastly different biological endpoint than the preceding hot spot analyses. The entire tumor section is potentially available for sampling, rather than only high areas of vascularity. Area-based algorithms have been developed initially for Automated Cellular Imaging Systems (Chromovision), followed by object-based counting by Aperio; see Potts, S. J., et al. "*Performance of a novel automated microvessel analysis algorithm across whole slide digital images*", Toxicologic Pathology. 2009, and more recently, object-based counting by other image analysis vendors like Definiens and Visiopharm. Where the literature has been studying in detail the intra-technique differences within hotspots (e.g. MVD versus Chalkey versus TVA) or more recently intra-technique differences between whole slide analysis (vessel counting versus vessel areas), there are no known studies that have asked whether hotspots themselves are a better technique versus overall vascularity with whole slide analysis.

The main endpoint used in MVD has been the number of vessels per square millimeter of tissue section. There are both theoretical and experimental problems with this endpoint. When one considers microvessel density from a stereological viewpoint, recognizing that a two-dimensional tissue section is only one sample from the three dimensional tumor, a number of theoretical problems present themselves. Anything observed on a section should be considered a profile, rather than the actual object. Recording the number of vessel profiles per area is not a measurement with roots in reality. Thicker or thinner sections, under or over staining, higher or lower cellularity in the sample, will all effect this endpoint. One violates all stereological considerations when trying to extrapolate this vessels per area measurement to volume, the best that the statistic can be used for is to compare the effect of one treatment with another, or before and after treatments, rather than as an absolute physical observation.

Experimentally, the difficulty with vessel densities is the ability to adequately number vessels with image analysis. In tumors with limited vascularity consisting of only small microcapillaries, it may be possibly, but as vascularity increases, it becomes difficult for the pathologist (and especially the computer) to determine which vessel profiles should be part of only one vessel. Many researchers resort to an area measurement to overcome this problem, the area of vessel profiles/area of tissue.

One should also return to the question of the end purpose when developing an analytical method. Is the goal to record how many vessels are in a given tissue, or is the goal to evaluate what percentage of the tumor or tissue is accessible to the vascular network? The named applicant has looked at the addition of a perimeter statistic on vessels, as a possible better correlate with oxygenation than number of vessels, but this requires a high degree of computer accuracy in identifying individual vessels. This assumes that large, non-oxygenating vessels are removed (an important software quality control technique recommended by the applicant) and also still suffers from the challenge of adequately assigning endothelial cells to vessel counts.

The existing microvessel density techniques reviewed above each suffers from the difficult of computationally assigning cells to vessels. This difficulty has resulted in limited usage of these techniques in clinical samples. Another disadvantage is that these techniques report the number or area of vessels, when biologically what may be more appropriate is the percentage of a given cell type that is actually near a vessel.

SUMMARY

In the disclosed methods, the central question is what percentage of the cells of interest are near a vessel, rather than the number of vessels themselves. The degree that a given cell or tissue is oxygenated or under hypoxic conditions will be driven not by the number of vessels but by the distance the tissue or cell is to the nearest vessel.

In one embodiment, endothelial cells or vessels are identified with one of many existing approaches using image analysis; for example, immunohistochemistry stains, or immunofluorescence dyes, which are conventionally used to identify endothelial cells. Then, a perimeter is drawn computationally, for example a radial distance from these endothelial cells which form the vessels. The distance can be selected or input by a user. The percentage of target tissue that is within or outside of this distance is determined and reported. Either a single distance or multiple distances can be utilized.

In another embodiment, cells of interest are identified and the percentages of these cells that are near vessels are determined.

In a particular embodiment, multiple myeloma a dual immunohistochemistry method can be used, where one antibody with a colorimetric label is used to identify vasculature and the second antibody is used to identify myeloma cells. The percentage of myeloma cells within a given distance of vessels is then calculated.

BRIEF DESCRIPTION OF THE DRAWINGS

These and other features can be further understood upon a thorough review of the descriptions, and particularly when viewed in conjunction with the appended drawings, wherein.

DETAILED DESCRIPTION

Figure 1:
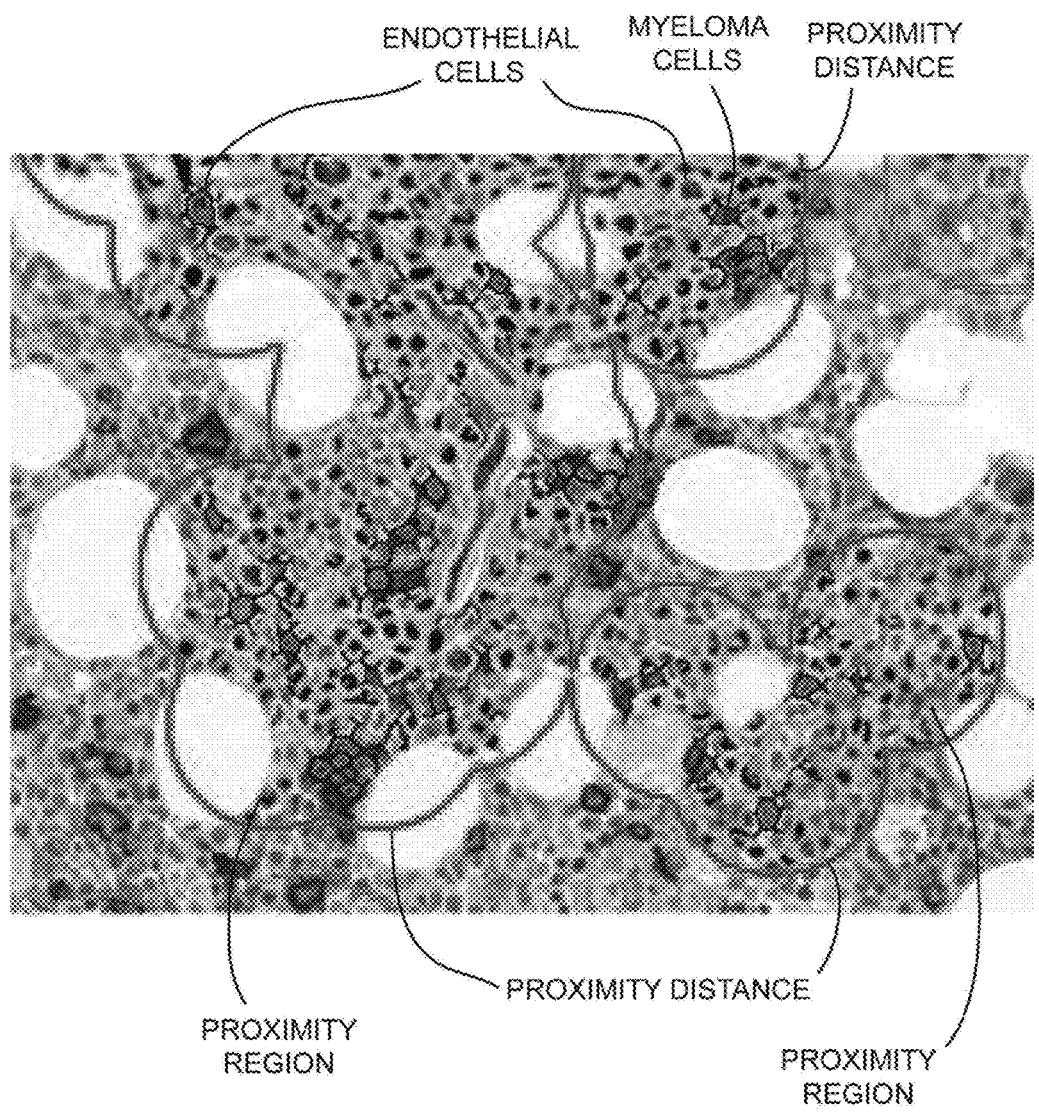
FIG. 1 shows a histology slide image used to analyze vascularity, the slide contains myeloma cells stained for colorimetric identification, and endothelial cells distinctly stained for colorimetric identification; a proximity distance perimeter is created at a distance from the endothelial cells for determining a composition of cells near a vascular object.

In the following description, for purposes of explanation and not limitation, details and descriptions are set forth in order to provide a thorough understanding of the embodiments of the invention. However, it will be apparent to those skilled in the art that the present invention may be practiced in other embodiments, including certain variations or alternative combinations that depart from these details and descriptions.

The methods disclosed herein are enhanced with certain aspects of the methods for feature analysis on consecutive tissue sections, as are described in commonly owned U.S. Pat. No. 8,787,651 issued Jul. 22, 2014; the contents of which are hereby incorporated by reference.

For purposes of this disclosure, the term "proximity analysis" refers to the determination of an amount of a first cellular entity that is within a given distance of a second distinct cellular entity;

"microvessel proximity analysis" refers to proximity analysis where one of the cellular entities comprises vascular cells;

"well-formed vessel" refers to a small artery, vein, or capillary that is easily viewed as a vessel on a histology section, these are frequently ones that have been cut orthogonally to the tissue section and will have well-formed lumen and typical "donut-like" annular morphology;

"vessel fragment" is used to refer to any of: (i) single endothelial cells that have not yet become vessels, (ii) microcapillaries of just a few endothelial cells, or (iii) a larger vessel that has been cut in such a way in histology that only a few cells and/or poorly formed morphology is present;

"random sampling" refers to a number of existing techniques for identifying regions of interest on a tissue section on which to make further measurements; and "whole section analysis" refers to utilizing the entire tissue section in order to make measurements, as opposed to select portions of the section.

In the general embodiments, the disclosed methods are performed using a computer with an electronic display. The computer can be any computer system that is programmed or otherwise configured to view and annotate digital images of tissue slides.

In a preferred embodiment, an amount of first antibodies that identify endothelial cells, such as certain immunohistochemistry stains or immunofluorescence dyes, are used to identify the endothelial cells within a tissue section. A second antibody stain or dye is used to identify other cells types of interest, or "target cells", within the tissue section. Image analysis is used to identify these endothelial cells, and optionally label them as either well-formed vessels or vessel fragments within an image of the tissue section.

Once the well-formed vessels or vessel fragments have been identified, a proximity distance from these objects is computationally formed on the slide-image. The distance can be presented as an image analysis mark-up, such as a series of contour lines surrounding the vessels at a distance therefrom. The proximity distance can be either entered or selected by the user, or calculated a number of other ways.

In an alternative embodiment, the proximity distance can be calculated as the average distance between vessels, and we can assume that half this distance is the leading edge of hypoxic conditions. The assumption is that vessels form to provide oxygenation to vessel in response to various cytokine and other factors, and thus are arranged so as to ensure adequate oxygenation.

A number of statistics can be used to measure vessel proximity. These include: (i) the percentage of cells that are within a given distance of vessels; (ii) the percentage of a given tissue area within a given distance of vessels (e.g. normal tissue, overall tissue, tumor tissue, stromal tissue, among other things). The average distance between vessels can also be used as a useful indicator.

Another aspect of vascularity analysis includes the evaluation of changes in the vessels. For example, a given angiogenesis treatment could either repair or disrupt the formation of normal vasculature. By evaluating changes to vessels, one can determine, for example, whether a given treatment is working. Vessel morphology is difficult to measure because only some vessels in any given tissue section are cut orthogonal to the section and thus are displayed in a way where vessel morphology can be calculated (e.g. cell wall thickness, diameter, vessel area, among others). It is suggested to assume that in any given tissue roughly the same number of vessels would be randomly sliced perpendicular to the section. Thus using only the well-formed vessels is an adequate sample for overall statistics for the population. This does assume that the vessel network is isotropic, that the blood vessels are not arranged in any consistent geometric pattern that would bias one randomly chosen direction from another.

Heterogeneity of vascularity can also be important. Vascularity can be measured by randomly sampling one or more tissue sections, and calculating heterogeneity on these measurements. The heterogeneity measurement may include ecology indices, or any form of simple or complex statistics that describe population variability (e.g. standard deviation, skewness, among others).

Now turning to the drawings, a method for measuring and reporting vascularity in a tissue sample includes the vascular proximity analysis of myeloma cells as shown in FIG. 1. As shown, myeloma cells are stained in a first color and endothelial cells are stained in a second color. A proximity distance is input into a computerized platform and resulting contour lines are formed about the slide-image. The percentage of myeloma cells within the proximity distance of vessels or vessel fragments is then computed.

Figure 2:
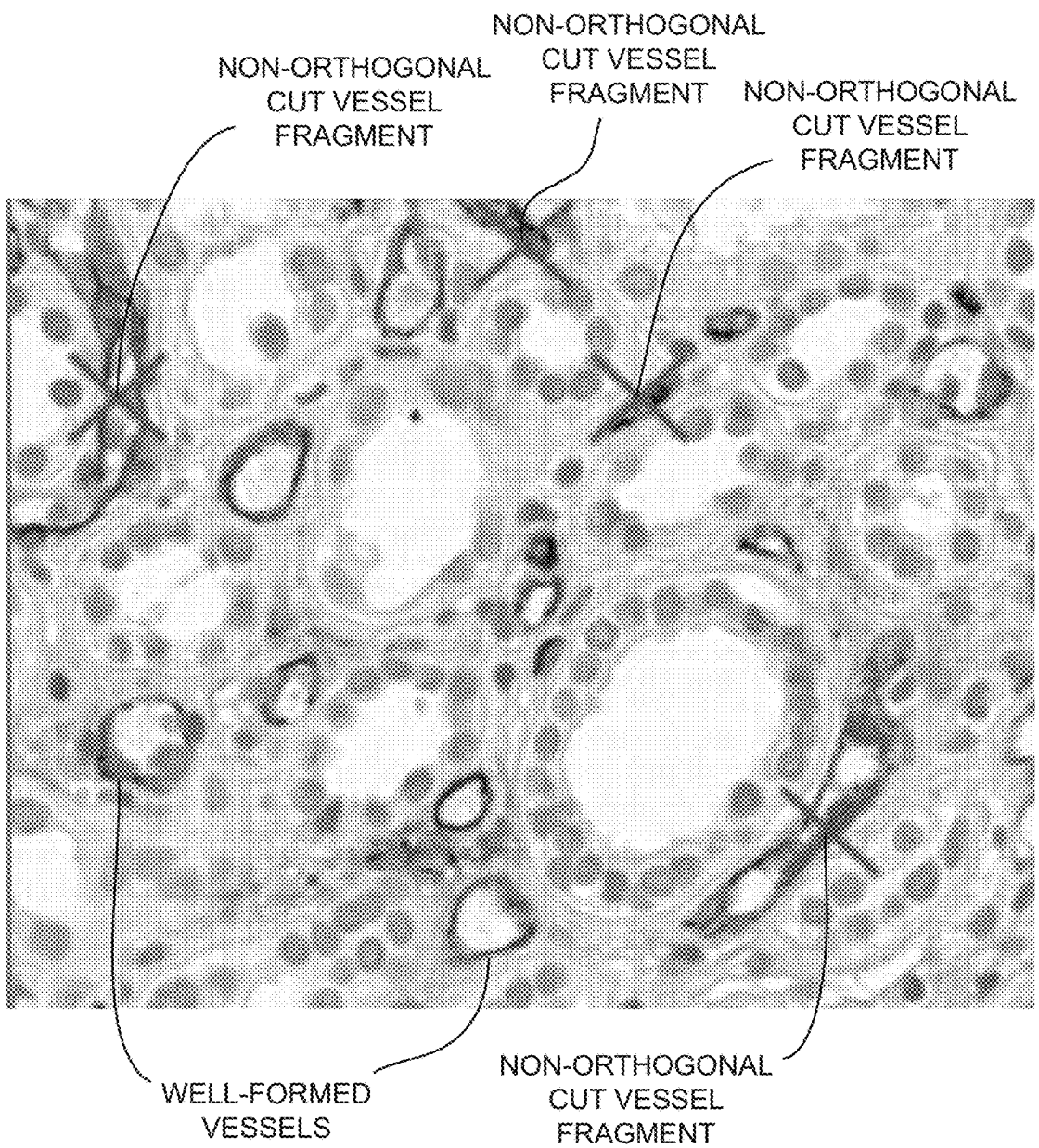
FIG. 2 shows a histology slide image used to analyze vascularity, wherein vessel portions not oriented orthogonal to the plane of sectioning of the imaged tissue section are omitted from quantitative analysis.

As described above, it may be preferred to include only well-formed vessels in the quantitative analysis. Thus, FIG. 2 shows a slide image wherein endothelial cells are stained, and a computer is used to identify those endothelial tissues which form an annular shape. Any regions of endothelial tissue that fail to form an annular shape are excluded from the analysis.

Thus, in an embodiment, a method for measuring and reporting vascularity in a biological tissue sample includes: (i) obtaining one or more tissue sections from the tissue sample; (ii) staining each of the tissue sections with: a first stain or dye for visually differentiating endothelial cells, lymphatic cells, or a combination thereof within the tissue section, and at least a second stain or dye for visually differentiating target cells, the target cells not including endothelial cells or lymphatic cells; (iii) acquiring at least a first digital image, the first digital image capturing at least a portion of a first tissue section of the stained tissue sections; and (iv) with the first digital image of the first tissue section or portion thereof: detecting at least one of: fully formed vessels and vessel fragments using visual characteristics associated with the first stain or dye; mapping about the first digital image one or more first proximity regions, each of the first proximity regions comprising an area between the detected vessels and a first distance outwardly therefrom; detecting the target cells using visual characteristics associated with the second stain or dye; calculating a vessel proximity score comprising a composition of the detected target cells that are disposed within the first proximity regions; and recording the vessel proximity score.

The first distance can be an average distance between adjacent detected vessels within the first digital image; or a user-defined distance.

In another embodiment, the method further comprises: with the first digital image of the first tissue section or portion thereof: annotating one or more regions of interest within the first digital image; calculating a vascular heterogeneity score comprising one or more of: a standard deviation, ecology indices, skewness, or a combination thereof; and recording the vascular heterogeneity score.

In another embodiment, the method further comprises: of the fully formed vessels and vessel fragments detected within the first digital image: digitally omitting any vessel fragments that fail to represent annular structure from the vessel proximity score as being non-orthogonal to a plane of the respective tissue section. The method may further comprise: with the first digital image of the first tissue section or portion thereof: calculating at least one of: vessel area, vessel wall thickness, diameter, lumen area, or a combination thereof; and recording with the vessel proximity score. Optionally, the method may further comprise: using the vessel proximity score and recorded data associated with the first digital image and that of a second digital image, the first digital image representing a first tissue section associated with treatment of a first angiogenesis-related therapy, the second digital image representing a second tissue section associated with treatment of a second angiogenesis-related therapy: (i) comparing the efficacy of the first angiogenesis-related therapy with another; (ii) determining whether a patient would benefit from one of the first and second therapy; or (iii) determining whether a patient is likely to have toxicity effects related to one of the first and second angiogenesis-related therapy.

In certain embodiments, each of the target cells, endothelial cells, and lymphatic cells are visually isolated using one of: immunohistochemistry (IHC), immunofluorescence (IF), DNA in situ hybridization (DNA-ISH), RNA in situ hybridization (RNA-ISH), or a combination thereof.

In an embodiment, the vessel proximity score comprises a percentage of the detected target cells that are disposed within the first proximity regions.

In another embodiment, the vessel proximity score comprises a tissue hypoxia score, wherein the tissue hypoxia score comprises a percentage of tissue disposed outside of the first proximity regions.

In another embodiment, the vessel proximity score comprises a tissue hypoxia score, wherein the tissue hypoxia score comprises a percentage of tissue disposed within the first proximity regions.

In certain embodiments, the tissue sections can comprise one or more tissue microarray samples.

In certain embodiments, the vessels the vessels can be detected using DNA or RNA in situ hybridization (ISH) for differentiating endothelial cells.

In an embodiment, the target cells can comprise first target cells and second target cells, the first target cells being distinct from the second target cells, and the first and second target cells not including endothelial cells; and the at least a second stain or dye for differentiating the target cells comprises: the second stain or dye for differentiating the first target cells, and a third stain or dye for differentiating the second target cells. Optionally, the method may further include: calculating a first vessel proximity score for the first target cells; calculating a second vessel proximity score for the second target cells; and recording the first and second vessel proximity scores.

In another embodiment, the target cells comprise one of: bone or fat cells; and the second stain or dye for differentiating the target cells comprises a stain or dye configured to isolate the bone or fat cells.

In yet another embodiment, the target cells comprise tumor cells; and the second stain or dye for differentiating the target cells comprises a stain or dye configured to isolate the tumor cells.

Certain embodiments may further include: of the fully formed vessels and vessel fragments detected within the first digital image: digitally omitting from the vessel proximity score any detected vessels having a diameter or vessel area greater than a maximum vessel size.

In yet another embodiment, a method for measuring and reporting vascularity in a biological tissue sample includes: obtaining one or more tissue sections from the tissue sample; staining each of the tissue sections with: a first stain or dye for differentiating endothelial cells, lymphatic cells, or a combination thereof; acquiring at least a first digital image, the first digital image capturing at least a portion of a first tissue section of the stained tissue sections; with the first digital image of the first tissue section or portion thereof: detecting at least one of: fully formed vessels and vessel fragments using visual characteristics associated with the first stain or dye; mapping about the first digital image one or more first proximity regions, each of the first proximity regions comprising an area between the detected vessels and a first distance outwardly therefrom; detecting tissue outside of the detected vessels; calculating a tissue hypoxia score, wherein the tissue hypoxia score comprises one of: a percentage of the tissue disposed outside of the first proximity regions, or a percentage of the tissue disposed within the first proximity regions; and recording the tissue hypoxia score.

REFERENCES

1. Brem, S., R. Cotran, and J. Folkman, *Tumor angiogenesis: a quantitative method for histologic grading*. Journal of the National Cancer Institute, 1972. 48(2): p. 347-356.
2. Weidner, N., et al., *Tumor angiogenesis and metastasis—correlation in invasive breast carcinoma*. New England Journal of Medicine, 1991. 324(1): p. 1-8.
3. Chalkley, H., *Method for the quantitative morphologic analysis of tissues*. Journal of the National Cancer Institute, 1943. 4(1): p. 47-53.
4. Fox, S. B., et al., *Tumor angiogenesis in node-negative breast carcinomas—relationship with epidermal growth factor receptor, estrogen receptor, and survival*. Breast cancer research and treatment, 1994. 29(1): p. 109-116.
5. Uzzan, B., et al., *Microvessel Density as a Prognostic Factor in Women with Breast Cancer A Systematic Review of the Literature and Meta-Analysis*. Cancer research, 2004. 64(9): p. 2941-2955.
6. Martin, L., et al., *Examining the technique of angiogenesis assessment in invasive breast cancer*. British journal of cancer, 1997. 76(8): p. 1046.
7. Van der Laak, J., et al., *An improved procedure to quantify tumor vascularity using true color image analysis: comparison with the manual hot-spot procedure in a human melanoma xenograft model*. J. Pathol, 1998. 184: p. 136-143.
8. Belien, J., et al., *Fully automated microvessel counting and hot spot selection by image processing of whole tumour sections in invasive breast cancer*. Journal of clinical pathology, 1999. 52(3): p. 184-192.
9. Offersen, B., M. Borre, and J. Overgaard, *Quantification of angiogenesis as a prognostic marker in human carcinomas: a critical evaluation of histopathological methods for estimation of vascular density*. European Journal of Cancer, 2003. 39(7): p. 881-890.
10. Sharma, S., M. Sharma, and C. Sarkar, *Morphology of angiogenesis in human cancer: a conceptual overview, histoprognostic perspective and significance of neoangiogenesis*. Histopathology, 2005. 46(5): p. 481-489.
11. Hansen, S., et al., *Angiogenesis in breast cancer: a comparative study of the observer variability of methods for determining microvessel density*. Laboratory investigation; a journal of technical methods and pathology, 1998. 78(12): p. 1563.
12. Fox, S. B., et al., *Quantitation and prognostic value of breast cancer angiogenesis: comparison of microvessel density, Chalkley count, and computer image analysis*. The Journal of pathology, 1995. 177(3): p. 275-283.
13. Korkolopoulou, P., et al., *Clinicopathologic correlations of bone marrow angiogenesis in chronic myeloid leukemia: a morphometric study*. Leukemia, 2003. 17(1): p. 89-97.
14. Korkolopoulou, P., et al., *A morphometric study of bone marrow angiogenesis in hairy cell leukaemia with clinicopathological correlations*. British journal of haematology, 2003. 122(6): p. 900-910.
15. Safali, M., et al., *A distinct microvascular pattern accompanied by aggressive clinical course in breast carcinomas: A fact or a coincidence?* Pathology-Research and Practice, 2010. 206(2): p. 93-97.
16. Van Niekerk, C. G., et al., *Computerized whole slide quantification shows increased microvascular density in pT2 prostate cancer as compared to normal prostate tissue*. The Prostate, 2009. 69(1): p. 62-69.
17. Bigler, S. A., R. E. Deering, and M. K. Brawer, *Comparison of microscopic vascularity in benign and malignant prostate tissue*. Human pathology, 1993. 24(2): p. 220-226.
18. Hlatky, L., P. Hahnfeldt, and J. Folkman, *Clinical application of antiangiogenic therapy: microvessel density, what it does and doesn't tell us*. J Natl Cancer Inst, 2002. 94(12): p. 883-93.
19. Potts, S. J., et al. *Performance of a novel automated microvessel analysis algorithm across whole slide digital*

*images.* in TOXICOLOGIC PATHOLOGY. 2009. SAGE PUBLICATIONS INC, THOUSAND OAKS, Calif. 91320 USA.

What is claimed is:

1. A method for measuring and reporting vascularity in a biological tissue sample, comprising:
    acquiring at least one digital image of a stained tissue section, wherein the stained tissue section is stained in such a manner to allow identification of at least one vessel object and at least one tissue object;
    detecting within the at least one digital image at least one vessel object, wherein the vessel object is selected from the group consisting of fully formed vessels and vessel fragments;
    detecting at least one tissue object within the digital image;
    calculating a vessel proximity score based on the detected vessel object and tissue object; and
    digitally omitting from the vessel proximity score any detected vessels having a diameter or vessel area greater than a maximum vessel size.

2. The method of claim 1, wherein the stained tissue section is stained using a histologic technique, wherein the histologic technique is selected from the group consisting of immunohistochemistry, immunofluorescence, DNA in situ hybridization, and RNA in situ hybridization.

3. The method of claim 1, wherein the vessel proximity score comprises a percentage of the detected target cells that are disposed within a first proximity region.

4. The method of claim 1, the vessel proximity score comprises a tissue hypoxia score, wherein the tissue hypoxia score comprises a percentage of tissue disposed outside of a first proximity region.

5. The method of claim 1, the vessel proximity score comprises a tissue hypoxia score, wherein the tissue hypoxia score comprises a percentage of tissue disposed within the first proximity region.

6. The method of claim 1, wherein the vessel proximity score uses a distance selected from the group consisting of an average distance between adjacent detected vessels within the digital image and a user-defined distance.

7. The method of claim 1, further comprising digitally omitting any vessel fragments that fail to represent annular structure from the vessel proximity score as being non-orthogonal to a plane of the respective tissue section.

8. The method of claim 1, further comprising calculating at least one vessel characteristic selected from the group consisting of vessel area, vessel wall thickness, diameter, and lumen area.

9. The method of claim 8, further comprising comparing the efficacy of a first angiogenesis-related therapy with a angiogenesis-related therapy based on the vessel proximity score and the at least one vessel characteristic.

10. The method of claim 9, further comprising determining if a patient would benefit from one of the first and second therapy.

11. The method of claim 8, further comprising determining if a patient is likely to have toxicity effects related to one of the first and second angiogenesis-related therapy.

12. The method of claim 1, further comprising calculating a vascular heterogeneity score using a method selected from the group consisting of standard deviation, ecology indices, and skewness.

13. The method of claim 1, comprising detecting the vessels using DNA or RNA in situ hybridization for differentiating endothelial cells.

14. The method of claim 1, wherein the cells are divided into at least two groups consisting of first cells and second cells.

15. The method of claim 14, further comprising:
    calculating a first vessel proximity score for the first cells; and
    calculating a second vessel proximity score for the second cells.

16. The method of claim 1, wherein the cells comprise tumor cells, and wherein the stained tissue sample differentiates the tumor cells.

\* \* \* \* \*